(12) United States Patent
Takahashi et al.

(10) Patent No.: US 6,660,888 B2
(45) Date of Patent: Dec. 9, 2003

(54) PROCESS FOR PRODUCING RETINOL AND INTERMEDIATE COMPOUNDS FOR PRODUCING THE SAME

(75) Inventors: Toshiya Takahashi, Ibaraki (JP); Shinzo Seko, Toyonaka (JP); Kazutaka Kimura, Ibaraki (JP); Noriyuki Doi, Ibaraki (JP); Naoto Konya, Takatsuki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/978,691

(22) Filed: Oct. 18, 2001

(65) Prior Publication Data

US 2002/0058844 A1 May 16, 2002

(30) Foreign Application Priority Data

| Oct. 18, 2000 | (JP) | ........................................ | 2000-317546 |
| Oct. 18, 2000 | (JP) | ........................................ | 2000-317547 |
| Oct. 18, 2000 | (JP) | ........................................ | 2000-317548 |
| Oct. 18, 2000 | (JP) | ........................................ | 2000-317549 |

(51) Int. Cl.$^7$ ..................... C07C 315/00; C07C 317/10; C07C 35/18
(52) U.S. Cl. ......................................... 568/32; 568/824
(58) Field of Search ........................... 568/28, 32, 700, 568/822, 823, 824, 825, 826

(56) References Cited

U.S. PATENT DOCUMENTS

| 4,175,204 A | 11/1979 | Babler | |
| 4,825,006 A | 4/1989 | Otera et al. | |
| 4,876,400 A | 10/1989 | Otera et al. | |
| 4,947,001 A | 8/1990 | Onishi et al. | |
| 5,053,552 A | 10/1991 | Mori et al. | |
| 5,449,836 A | * 9/1995 | Chabardes | .................. 568/591 |
| 6,211,411 B1 | * 4/2001 | Takahashi | .................... 568/31 |
| 6,297,402 B1 | * 10/2001 | Takahashi et al. | ............ 568/28 |

FOREIGN PATENT DOCUMENTS

| EP | 0 900 785 A2 | 3/1999 |
| EP | 1 085 008 A1 | 3/2001 |
| EP | 1 125 921 A1 | 8/2001 |

OTHER PUBLICATIONS

Uneyama et al., Chemistry Letters, pp. 39–40, (1977).
Mandai et al., Tetrahedron Letters, vol. 23, No. 45, pp. 4721–4724, (1982).
Manchand, et al., Helvetica Chimica Acta, vol. 59, Fasc. 2, No. 44, pp. 387–396, (1976).
Yamano et al., J. Chem. Soc. Perkin Trans., No. 1, pp. 1599–1610, (1993).
Mercier et al., Pure & Appl. Chem, vol. 66, No. 7, pp. 1509–1518, (1994).
Torii et al., Chemistry Letters, pp. 479–482, (1975).

* cited by examiner

Primary Examiner—Jean F. Vollano
(74) Attorney, Agent, or Firm—Birch, Stewart, Kolasch & Birch, LLP

(57) ABSTRACT

There are disclosed a disulfone compound of formula (1):

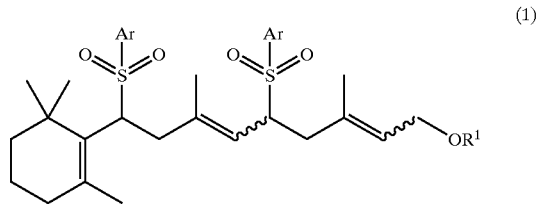

(1)

wherein Ar denotes an aryl group that may have a substituent, R1 denotes a hydrogen atom or a protective group of a hydroxyl group and the wavy line means that the disulfone compound is an E or Z geometrical isomer or a mixture thereof,
  a method for producing the same,
  intermediate compounds therefore and
  a process for producing retinol through the disulfone compound.

30 Claims, No Drawings

PROCESS FOR PRODUCING RETINOL AND INTERMEDIATE COMPOUNDS FOR PRODUCING THE SAME

FIELD OF THE INVENTION

The present invention relates to sulfone compounds that are useful intermediate compounds for the production of pharmaceuticals, feed additives or food additives such as retinol, and production methods for producing the same, and a process for the production of retinol using the same.

BACKGROUND OF THE INVENTION

There has been disclosed a process for producing retinol by reacting a sulfone of formula (6) shown below with a C10 aldehyde compound derived from linalool by a plurality of steps to obtain a C20 hydroxy sulfone compound, and derivatizing the same by a plurality of steps (U.S. Pat. No. 4,825,006). However, there is a demand for the development of a further improved industrial production process for producing retinol.

SUMMARY OF THE INVENTION

According to the present invention, retinol can be readily obtained by using novel sulfone compounds and a readily available C5 allyl halide compound.

The present invention provides 1. a disulfone compound of formula (1):

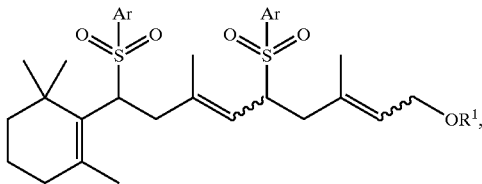

(1)

wherein Ar denotes a substituted or unsubstituted aryl group, $R^1$ denotes a hydrogen atom or a protective group of a hydroxyl group and the wavy line means that the disulfone compound is an E or Z geometrical isomer or a mixture thereof;

2. a process for producing the disulfone compound of formula (1) as defined above, which comprises reacting an allylsulfone of formula (2):

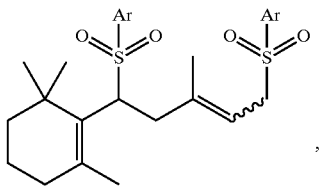

(2)

wherein Ar and the wavy line have the same meanings as defined in connection with formula (1) above, with an allyl halide compound of formula (3):

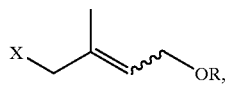

(3)

wherein X denotes a halogen atom, R denotes a protective group of a hydroxyl group and the wavy line has the same meanings as defined above, in the presence of a base selected from an alkyl lithium, an alkali metal alkoxide, an alkali metal amide, an alkali metal hydride, or an alkali metal hydroxide, and optionally deprotecting;

3. a process for producing retinol, which comprises reacting the disulfone compound of formula (1):

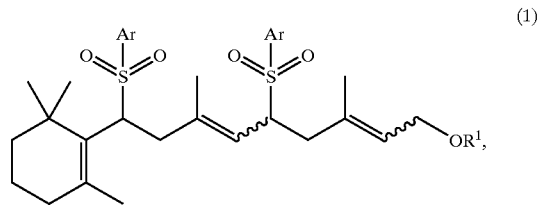

(1)

wherein Ar, $R^1$ and the wavy line have the same meaning as defined above, with a base selected from an alkali metal alkoxide, an alkali metal amide, an alkali metal hydride, or an alkali metal hydroxide, and optionally deprotecting;

4. an allylsulfone compound of formula (2):

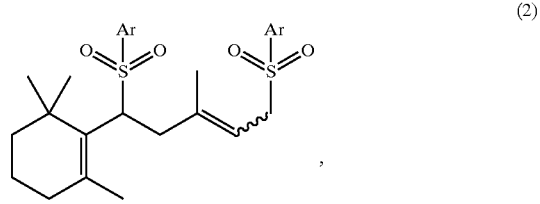

(2)

wherein Ar and the wavy line have the same meanings as defined above;

5. a process for producing an allylsulfone compound of formula (2) as defined above, which comprises reacting the sulfone compound of formula (4):

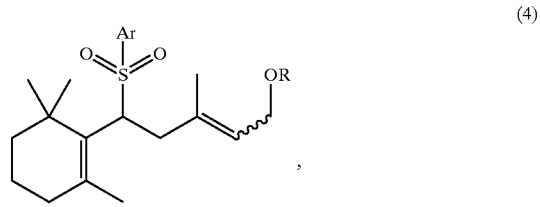

(4)

wherein R, Ar and the wavy line have the same meanings as defined above, with an arylsulfinate of formula (5):

ArSO₂M (5)

wherein Ar has the same meaning as defined above in connection with formula (1), and M denotes an alkali metal, in the presence of a palladium catalyst; and 6. a process for producing a sulfone of formula (4) as defined above, which comprises reacting a sulfone of formula (6):

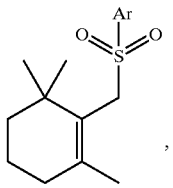

(6)

wherein Ar has the same meaning as defined above, with an allyl halide compound of formula (3):

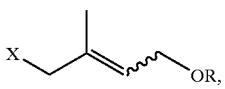

(3)

wherein X, R and the wavy line have the same meanings as defined above, in the presence of a base selected from an alkyl lithium, an alkali metal alkoxide, an alkali metal amide, or an alkali metal hydride.

DETAILED DESCRIPTION

A description will be made to the substituent groups in formulae (1) through (6).

Examples of the protective group represented by R1 or R in the present specification include, for example, an acyl group, a silyl group, tetrahydropyranyl group, an alkoxymethyl group (e.g. a methoxymethyl group, a methoxyethoxymethyl group and the like), 1-ethoxyethyl group, a p-methoxybenzyl group, a t-butyl group, a trityl group, and an alkoxy carbonyl group such as 2,2,2-trichloroethoxycarbonyl group, allyloxycarbonyl or the like.

Examples of the acyl group include, for example, a $C_1$–$C_6$ alkanoyl group, which may be substituted with a halogen atom or an alkoxy group, and a benzoyl group, which may be substituted with a halogen atom, a hydroxy group, an alkoxy group, an acetoxy group, a nitro group or the like.

Examples of the halogen atom include a fluorine atom, a chlorine atom, a bromine atom, and an iodine atom.

Specific examples of the $C_1$–$C_6$ alkanoyl group, which may be substituted with a halogen atom or an alkoxy group include, for example, a formyl, acetyl, ethoxyacetyl, fluoroacetyl, difluoroacetyl, trifluoroacetyl, chloroacetyl, dichloroacetyl, trichloroacetyl, bromoacetyl, dibromoacetyl, tribromoacetyl, propionyl, 2-chloropropionyl, 3-chloropropionyl, butyryl, 2-chlorobutyryl, 3-chlorobutyryl, 4-chlorobutyryl, 2-methylbutyryl, 2-ethylbutyryl, valeryl, 2-methylvaleryl, 4-methylvaleryl, hexanoyl, isobutyryl, isovaleryl, pivaloyl, or the like.

Examples of the benzoyl group, which may be substituted with a halogen atom, a hydroxy group, an alkoxy group, an acetoxy group, a nitro group or the like include, for example, a benzoyl, an o-chlorobenzoyl, m-chlorobenzoyl, p-chlorobenzoyl, o-hydroxybenzoyl, m-hydroxybenzoyl, p-hydroxybenzoyl, o-acetoxybenzoyl, o-methoxybenzoyl, m-methoxybenzoyl, p-methoxybenzoyl and p-nitrobenzoyl group.

Examples of the silyl group include, for example, a trimethylsilyl, triethylsilyl, t-butyldimethylsilyl, t-butyldiphenylsilyl group and the like.

Preferred protective group is an acyl group (e.g. acetyl group and the like).

Examples of the unsubstituted or substituted aryl group represented by "Ar" include, for example, a phenyl group and a naphthyl group, and a phenyl or naphthyl group substituted with a straight or branched C1–C5 alkyl group, a straight or branched C1–C5 alkoxy group, a halogen atom, a nitro group or the like.

Examples of the C1–C5 alkyl group include, for example, a methyl group, an ethyl group, a n-propyl group, an isopropyl group, a sec-butyl group, a t-butyl group, an isobutyl group, a n-pentyl group, a t-amyl group, and the like.

Examples of the C1–C5 alkoxy group include, for example, a methoxy group, an ethoxy group, a n-propoxy group, an isopropoxy group, a sec-butoxy group, a t-butoxy group, an isobutoxy group, a n-pentoxy group, a t-amyloxy group and the like.

Specific examples of the unsubstituted or substituted aryl group include, for example, phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl and p-nitrophenyl and the like. Preferred are a phenyl group, a tolyl group and the like.

The disulfone compound of formula (1) can be obtained, for example, by a process of reacting the allylsulfone compound of formula (2) with an allyl halide compound of formula (3) in the presence of a base selected from an alkyl lithium, an alkali metal alkoxide, alkali metal amide, alkali metal hydride or an alkali metal hydroxide.

Examples of the halogen atom represented by X in formula (3) typically include a chlorine atom, a bromine atom, and an iodine atom.

Specific examples of the allyl halide compound of formula (3) include, for example, an ally halide compound of formula (3), wherein X is a bromine atom, and R is an acetyl group.

Examples of the alkyl lithium include, for example, n-butyl lithium, sec-butyl lithium, t-butyl lithium and the like.

Examples of the alkali metal alkoxide include, for example, a C1–C5 alcoholate of an alkali metal such as sodium methoxide, potassium methoxide, lithium methoxide, sodium ethoxide, potassium ethoxide, lithium ethoxide, potassium t-butoxide, sodium t-butoxide, lithium t-butoxide, sodium t-amylate, potassium t-amylate and the like.

Examples of the alkali metal amide include, for example, lithium amide, potassium amide, sodium amide, lithium diisopropylamide, sodium hexamethyldisilazide, potassium hexamethyldisilazide, lithium hexamethyldisilazide and the like.

Examples of the alkali metal hydride include, for example, sodium hydride, potassium hydride, lithium hydride and the like.

Examples of the alkali metal hydroxide include, for example, sodium hydroxide, potassium hydroxide and lithium hydroxide.

Any bases selected from the alkyl lithium, alkali metal alkoxide, alkali metal amide, alkali metal hydride and alkali metal hydroxide may be used together. For example, sodium t-butoxide and sodium hydride may be used together. Furthermore, sodium t-butoxide may be produced, in situ, in the reaction mixture, from a combination of sodium hydride and t-butanol, and lithium diisopropyl amide can be produced from a combination of diisopropylamine and n-butyl lithium.

The amount of the base that may be used in the reaction is usually 0.5 to 3 moles per mol of the allylsulfone compound of formula (2).

The reaction is usually conducted in an organic solvent. Examples of the organic solvent that may be used include, for example, an aprotic polar solvent such as acetonitrile, N,N-dimethylformamide, hexamethylphosphoric triamide, sulfolane, 1,3-dimethyl-2-imidazolidinone, 1-methyl-2-pyrrolidinone, or the like, an ether solvent such as diethyl ether, tetrahydrofuran, 1,4-dioxane, dimethoxyethane, anisole, or the like, a hydrocarbon (aliphatic or aromatic) solvent such as n-hexane, cyclohexane, n-pentane, benzene, toluene and xylene. The solvent may be employed alone or as a mixture thereof.

The reaction temperature may be set within a range of from −78° C. to the boiling point of the solvent used.

Any suitable phase-transfer catalyst can be used to promote the reaction, if necessary.

Examples of the phase-transfer catalyst include, for example, quaternary ammonium salts, quaternary phosphonium salts, sulfonium salts and the like are mentioned. Preferred are quaternary ammonium salts.

Examples of quaternary ammonium salts include tetramethylammonium chloride, tetraethylammonium chloride, tetrapropylammonium chloride, tetrabutylammonium chloride, tetrapentylammonium chloride, tetrahexylammonium chloride, tetraheptylammonium chloride, tetraoctylammonium chloride, tetrahexadecylammonium chloride, tetraoctadecylammonium chloride, benzyltrimethylammoniumn chloride, benzyltriethylammonium chloride, benzyltributylammonium chloride, 1-methylpyridinium chloride, 1-hexadecylpyridinium chloride, 1,4-dimethylpyridiniium chloride, tetramethyl-2-butylammonium chloride, trimethylcyclopropylammonium chloride, tetramethylammonium bromide, tetraethylammonium bromide, tetrapropylammonium bromide, tetrabutylammonium bromide, tetrapentylammonium bromide, tetrahexylammonium bromide, tetraheptylammonium bromide, tetraoctylammonium bromide, tetrahexadecylammonium bromide, tetraoctadecylammonium bromide, benzyltrimethylammonium bromide, benzyltriethylammonium bromide, benzyltributylammonium bromide, 1-methylpyridinium bromide, 1-hexadecylpyridinium bromide, 1,4-dimethylpyridinium bromide, tetramethyl-2-butylammonium bromide, trimethylcyclopropylammonium bromide, tetramethylammonium iodide, tetrabutylammonium iodide, tetraoctylammonium iodide, t-butylethyldimethylammonium iodide, tetradecyltrimethylamsmonium iodide, hexadecyltrimethylammonium iodide, octadecyltrimethylammonium iodide, benzyltrimethylammonium iodide, benzyltriethylammonium iodide and benzyltributylammonium iodide and the like.

Examples of quaternary phosphonium salts include tributylmethylphosphonium chloride, triethylmethylphosphonium chloride, methyltriphenoxyphosphonium chloride, butyltriphenylphosphonium chloride, tetrabutylphosphonium chloride, benzyltriphenylphosphonium chloride, hexadecyltrimethylphosphonium chloride, hexadecyltributylphosphonium chloride, hexadecyldimethylethylphosphonium chloride, tetraphenylphosphonium chloride, tributylmethylphosphonium bromide, triethylmethylphosphonium bromide, methyltriphenoxyphosphonium bromide, butyltriphenylphosphonium bromide, tetrabutylphosphonium bromide, benzyltriphenylphosphonium bromide, hexadecyltrimethylphosphonium bromide, hexadecyltributylphosphonium bromide, hexadecyldimethylethylphosphonium bromide, tetraphenylphosphonium bromide, tributylmethylphosphonium iodide, triethylmethylphosphonium iodide, methyltriphenoxyphosphonium iodide, butyltriphenylphosphonium iodide, tetrabutylphosphonium iodide, benzyltriphenylphosphonium iodide, hexadecyltrimethylphosphonium iodide and the like.

Examples of sulfonium salts include dibutylmethylsulfonium chloride, trimethylsulfonium chloride, triethylsulfonium chloride, dibutylmethylsulfonium bromide, trimethylsulfonium bromide, triethylsulfonium bromide, dibutylmethylsulfonium iodide, trimethylsulfonium iodide and triethylsulfonium iodide and the like.

The amount of such a phase transfer catalyst that may be used is usually about 0.01 to about 0.2 moles, preferably about 0.02 to about 0.1 mol per mol of the allylsulfone compound (2).

The reaction is preferably conducted in the absence of oxygen, for example, in an inert gas atmosphere of nitrogen gas or argon gas. The solvent that may be used is preferably degassed prior to use. An antioxidant such as 3,5-di-t-butyl-4-hydroxytoluene (BHT), 2-&3-t-butyl-4-hydroxyanisole (BHA), vitamin E, ethoxyquin or the like may be preferably added in the reaction.

After completion of the reaction, the disulfone compound of formula (1) can be isolated by a usual post-treatment such as extraction, crystallization, various kinds of chromatography and/or the like. The disulfone compound of formula (1) wherein $R^1$ is a hydrogen atom may be produced by the reaction of alkali hydroxide, while a protective group R such as the acyl group being removed during the reaction. Alternatively, the protective group may be optionally deprotected by those suitable procedures as described below for the production of retinol, if desired, The disulfone compound of formula (1) can be converted to retinol by a process, which comprises reacting the disulfone compound of formula (1) with a base selected from an alkali metal alkoxide, an alkali metal amide, an alkali metal hydride, or an alkali metal hydroxide, and optionally deprotecting.

The same alkali metal alkoxide, alkali metal amide, alkali metal hydride, and alkali metal hydroxide as described above for the production process of the disulfone compound of formula (1) can be used in this reaction.

An amount of the base that may be used is usually 2 to 40 moles, preferably 5 to 30 moles per mol of the disulfone compound of formula (1). Preferably employed is the alkali metal hydroxide. Fine power alkali metal hydroxide is preferably used.

Alternatively, the reaction of the disulfone compound of formula (1) with a base is preferably conducted in the presence of a lower alcohol or the phase-transfer catalyst as described above.

Preferred phase-transfer catalyst is the quaternary ammonium salt, and suitable amount of the phase-transfer catalyst is 0.01 to 0.2 mol per mol of the disulfone compound of formula (1).

Examples of the lower alcohol include, for example, methanol, ethanol, isopropanol, n-propanol, n-butyl alcohol, s-butyl alcohol, t-butyl alcohol, ethylene glycol, ethylene glycol monomethyl ether, and the like.

An amount of the lower alcohol that may be used is usually 0.1 to 3 moles per mol of the disulfone compound of formula (1).

In the aforementioned reaction, the organic solvent that may be used in the process for producing the disulfone compound of formula (1) may be employed. Preferred is the hydrocarbon solvent as described above.

The reaction temperature is usually in the range from −30° C. to the boiling point of the solvent used, and preferred is the range from about 0 to about 50° C.

The reaction is preferably conducted in the absence of oxygen, for example, in an inert gas atmosphere of nitrogen gas or argon, and shielding from the light. The solvent that may be used is preferably degassed prior to use. An antioxidant such as 3,5-di-t-butyl-4-hydroxytoluene (BHT), 2-&3-t-butyl-4-hydroxyanisole(BHA), vitamin E, ethoxyquin or the like is preferably added in the reaction.

After completion of the reaction, retinol can be isolated by performing a usual post-treatment, or optional deprotection of the retinol having a protected hydroxy group.

For example, retinol can be obtained by the reaction of the disulfone of formula (1) having an acyl group as $R^1$, with a base such as alkali metal hydroxide, alkali metal hydride or the like.

Alternatively, retinol can be obtained, for example, by a suitable deprotecting procedure to remove the protective group R from the obtained retinol having a protected hydroxy group, which procedure includes an acid or base treatment, a treatment with tetraalkylammonium fluoride to remove a sily group, or similar methods as disclosed in Protective Groups in Organic Synthesis, Greene, T. W. $3^{rd}$ Edition, Wiley, the whole disclosure of which is incorporated herein by reference.

Retinol is tropically purified in a protected form, by crystallization, various kinds of chromatography and/or the like, if necessary. Protected retinol may be produced by introducing any suitable protective group such as an acetyl group or the like in a conventional manner (e.g. JP4-3391B, or the reference as described above).

Next a description will be made to a process for producing the allylsulfone compound of formula (2), which can be used for producing the disulfone compound of formula (1). The production process for producing the allylsulfone compound of formula (2) comprises reacting the sulfone compound of formula (4) with the arylsulfinate of formula (5) in the presence of a palladium catalyst.

In the arylsulfinate of formula (5), examples of the alkali metal represented by M include, for example, lithium, sodium or potassium.

The substituted or unsubstituted aryl group represented by Ar in formula (5) is described above.

Examples of the arylsulfinate include, for example, lithium, sodium, or potassium arylsulfinate, Specific examples thereof include, for example, sodium benzensulfinate, sodium 1-naphthalensulfinate, sodium 2-naphthalenesulfinate, sodium o-, m- or p-toluenesulfinate, sodium o-, m-, or p-metoxybenzenesulfinate, sodium o-, m-, or p-chlorobenzenesulfinate, sodium o, m-, or p-bromobenzenesulfinate, sodium o-, m-, or p-iodobenzenesulfinate, sodium o-, m, or p-fluorobenzenesulfinate, sodium o-, m-, or p-nitrobenzenesulfinate, and sulfinate salts having lithium or potassium in place of the sodium in the sodium sulfinates described above.

Preferred are sodium benzensulfinate, potassium benzenesulfinate, sodium p-toluenesulfinate, potassium p-toluenesulfinate and the like. The arylsulfinate salt that contains crystal water may be used in the reaction.

The amount of arylsulfinate of formula (5) is usually about 1 to about 3 moles per mol of the sulfone (4).

Examples of the palladium catalyst include, for example, tetrakis (triphenylphosphine) palladium, allyl chloride palladium dimer, palladium acetate, palladium oxide, palladium chloride, palladium hydroxide, palladium propionate, dichlorobis(triphenylphosphine) palladium, di -$\mu$-chlorobis (η-allyl) palladium, dichloro(η-1,5-cyclooctadiene) palladium, dichloro(η-2,5-norbornadiene) palladium, dichlorobis(acetonitrile) palladium, dichlorobis (benzonitrile) palladium, dichlorobis(N,N-dimethylformamide) palladium, bis(acetylacetonato) palladium, palladium charcoal and the like.

The amount of the palladium catalyst is usually 0.001 mol % to 20 mol % per mol of the sulfone compound of formula (4).

A suitable ligand can be used in the reaction. Examples of the ligand include, for example, a phosphrous ligand such as a phosphine ligand, a phosphite ligand or the like.

Examples of the phosphine ligand include, for example, triarylphosphines, trialkylphosphines and tris(dialkylamino) phosphines, which may have a substituent, and the like. Examples of the phosphite ligand include, for example, trialkylphosphite, triarylphosphite and the like.

Specific examples thereof include, for example, triphenylphosphine, tri-t-butylphosphine, tricyclohexylphosphine, dicyclohexylphenylphosphine, dicyclohexyl-o-tolylphosphine, dicyclohexyl-m-tolylphosphine, dicyclohexyl-p-tolylphosphine, dicyclohexyl-o-anisylphosphine, dicyclohexyl-o-biphenylphosphine, diadamantyl-n-butylphosphine, tri-o-tolylphosphine, tri-m-tolylphosphine, tri-p-tolylphosphine and tris(dimethylamino)phosphine, triphenylphosphite, tri-p-tolylphosphite, tri-m-tolylphosphite, tri-o-tolylphosphite, trimethylphosphite, triethylphosphite, triisopropylphosphite, tri-t-butylphosphite, tris(tridecyl) phosphite, tris(2,4-di-t-butylphenyl)phosphite and the like. The phosphorous ligand may be added separately to the palladium catalyst that does not contain the phosphorous ligand.

The amount the phosphrous ligand that may be used is usually in the range from 1 mol % to 20 mol % per mol of palladium metal.

In this process a base compound or an acid compound is preferably used as an auxiliary agent to promote the reaction more smoothly, thereby the amount of the expensive palladium can be reduced.

Examples of the amine include, for example, a mono-, di-, or tri-(C2–C6)alkyl amine, a secondary or tertiary cyclic amine, a primary, secondary or tertiary aryl amine.

Specific examples thereof include, for example, ethylamine, n-propylamine, isopropylamine, n-butylamine, sec-butylamine, t-butylamine, n-pentylamine, n-hexylamine, cyclohexylamine, aniline, o-, m-, or p-anisidine, 4-n-butylaniline, diethylamine, diisopropylamine, di-n-butylamine, di-n-hexylarnine, pyrrolidine, piperidine, morpholine, N-methylaniline, N-ethylaniline, N-n-butylaniline, N-methyl-p-anisidine, diphenylamine, triethylamine, tri-n-propylamine, triisopropylamine, N,N-diisopropylethylamine, tri-n-butylamine, triisobutylamine, tri-n-pentylamine, tri-n-hexylamine, N-methylpyrrolidine, N-methylpiperidine, N-ethylpiperidine, N-methylmorpholine, triphenylamine, and ethylenediamine,N,N,N',N'-tetramethylethylene diamine.

Examples of the acid compound include, a carboxylic acid (e.g. C1–C3 carboxylic acid such as formic acid, acetic acid, propionic acid, oxalic acid, or the like), halo- or nitro-substituted benzoic acid such as p-nitrobenzoic acid, p-chlorobenzoic acid or the like.

In the above reaction, an organic solvent is usually used. Examples of a solvent to be used include, for example, an ether solvent such as diethyl ether, tetrahydrofuran, 1,4-dioxane, dimethoxyethane, anisole or the like, an alcohol solvent such as methanol, ethanol, 2-propanol, t-butanol or the like, an aprotic polar solvent such as acetonitrile, N,N-dimethylformamide, hexamethylphosphoric triamide, sulfolane, 1,3-dimethyl-2-imidazolidinone, 1-methyl-2-pyrrolidinone or the like, and a hydrocarbon (aliphatic or aromatic) solvent such as n-hexane, cyclohexane, n-pentane, benzene, toluene, xylene or the like. These may be employed alone or as a mixture thereof.

The reaction temperature may be optionally selected in the range from −78° C. to the boiling point of the solvent used, and preferred is the range from about 20 to about 100° C. The allylsulfone derivative (2) can be produced by performing, after the reaction, usual post-treatment, such as washing with water, extraction, crystallization and various kinds of chromatography.

The sulfone compound of formula (4) can be produced by a process, which comprises reacting the sulfone compound of formula (6) with the allyl halide compound of formula (3) in the presence of a base selected from an alkyl lithium, an alkali metal alkoxide, an alkali metal amide, or an alkali metal hydride.

The alkyl lithium, alkali metal alkoxide, alkali metal amide, or alkali metal hydride as described for the processes above can be used in this reaction. Preferred bases are the alkyl lithium (e.g. n-butyl lithium, s-butyl lithium, t-butyl lithium, and the like), the alkali metal alkoxide (e.g. sodium methoxide, potassium methoxide, potassium t-butoxide, sodium t-butoxide and the like).

The alkali metal hydride is preferably used together with an auxiliary agent, which include, for example, an alcohol such as n-butyl aclcohol, s-butyl alcohol, t-butyl alcohol, t-amyl alcohol or the like, an amine such as aniline, diisopropylamine or the like, a sulfone such as dimethylsulfone or the like, a sulfoxide such as dimethylsulfoxide or the like, and a mixture thereof The amount of the auxiliary agent is usually 0.1 to 3 moles per mol the sulfone (6). The auxiliary agent can be used as a solvent.

Furthermore, an anion activating agent such as a crown ether, tetramethylethylenediamine or the like may be added in the reaction, or an allyl halide activating agent such as sodium iodide, tetrabutylammonium iodide, or the like may be added.

The amount of the base that may be used is usually about 0.5 to about 3 moles per mol of the sulfone (6).

In the aforementioned reaction, an organic solvent is usually used. The solvent as described above for the production process of the disulfone compound of formula (1) can be employed in this reaction.

The reaction is preferably conducted in the absence of oxygen, for example, in an inert gas atmosphere of nitrogen gas or argon. The solvent that may be used is preferably degassed prior to use. An antioxidant such as 3,5-di-t-butyl-4-hydroxytoluene (BHT), 2-&3-t-butyl-4-hydroxyanisole (BHA), vitamin E, ethoxyquin or the like may be preferably added in the reaction.

After completion of the reaction, the sulfone compound of formula (4) can be isolated by a usual post-treatment such as extraction, crystallization, chromatographies or the like.

The sulfone of formula (6) can be readily produced according to the description of Chem. Lett. 479 (1975), and the allyl halide compound of formula (3) can be readily produced by a method described in U.S. Pat. No. 4,175,204.

EXAMPLES

The present invention will be explained by way of examples, but are not to be construed to limit the invention thereto.

Example 1

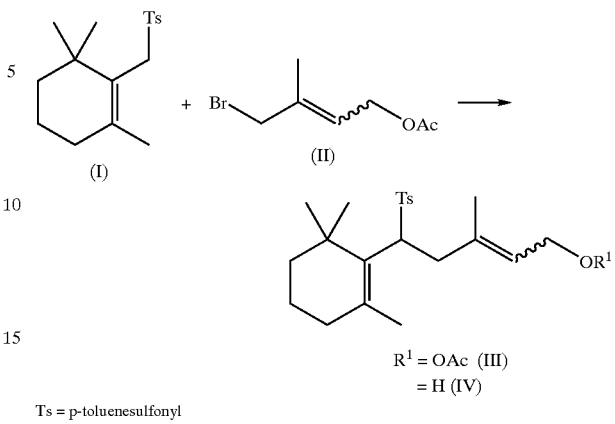

Ts = p-toluenesulfonyl

A solution of 224 mg (2 mmol) of potassium t-butoxide in 6 ml of N,N-dimethylformamide (DMF) was cooled to −60° C., and then a solution of 585 mg (2 mmol) of sulfone (I) in DMF (4 ml) was added dropwise over 20 seconds. Subsequently, a solution of 215 mg (1 mmol, purity 96%) of allyl halide (II) in DMF (4 ml) was added dropwise at the same temperature over 5 minutes and was stirred at the same temperature for 3 hours. After the reaction, the reaction solution was poured into a saturated aqueous ammonium chloride solution and was extracted with ethyl acetate. The organic layer obtained was washed with an aqueous saturated sodium hydrogencarbonate solution and an aqueous saturated sodium chloride solution sequentially, and was dried with anhydrous magnesium sulfate. Thereafter, the solvent was removed by distillation to give a crude yellow oil product. High performance liquid chromatography analysis showed that sulfone compound(III) and (IV) were obtained in a yield of 71.2% and 15.4% respectively.

Sulfone (III)

$^1$H-NMR δ (CDCl$_3$); 0.73(3H, s), 0.99(3H, s), 1.25–1.64 (7H, m), 1.97–2.04(8H, m), 2.37(3H, m), 2.54–2.96(3H, m), 3.74–3.87(1H, m), 4.37(2H, d, J=7 Hz), 5.29(1H, t, J=7 Hz), 7.23(2H, d, J=8 Hz), 7.69(2H, d, J=8 Hz)

Sulfone (IV)

$^1$H-NMR δ (CDCl$_3$); 0.82(3H, s), 1.04(3H, s), 1.22–1.57 (4H, m), 1.30(3H, s), 2.00(3H, s), 2.03–2.24(2H, m), 2.33 (1H, br. S), 2.42(3H, m), 2.59(1H, dd, J=7 Hz, 14 Hz), 2.99(1H, dd, J=7 Hz, 14 Hz), 3.91(1H, t, J=7 Hz), 3.99(2H, d, J=7 Hz), 5.40(1H, t, J=7 Hz), 7.31(2H, d, J=8 Hz), 7.75(2H, d, J=8 Hz)

Example 2

A solution of 224 mg (2 mmol) of potassium t-butoxide in 6 ml of DMF was cooled to −20° C., and then a solution of 585 mg (2 mmol) of sulfone (I) in DMF (4 ml) was added dropwise over 20 seconds, then maintained for 5 minutes and thereafter cooled to −60° C. Subsequently, a solution of 215 mg (1 mmol, purity 96%) of allyl halide (II) in DMF (3 ml) was added dropwise thereto at the same temperature over 5 minutes and was stirred for 3 hours. After the reaction, the resultant was poured into a saturated aqueous ammonium chloride solution and was extracted with ethyl acetate. The organic layer obtained was washed with a saturated aqueous sodium hydrogencarbonate solution and a saturated aqueous sodium chloride solution sequentially, and was dried with anhydrous magnesium sulfate. Thereafter, the solvent was removed by distillation to give a crude yellow oil product.

The amount of the crude product was measured by HPLC to show that the yield of sulfone compound (III) was 99.5%.

Example 3

A solution of 116 mg (1.2 mmol) of sodium t-butoxide in 6 ml of DMF was cooled to 0° C., and then a solution of 876 mg (3 mmol) of sulfone (I) in DMF (4 ml) was added dropwise thereto over 20 seconds, and the resulting mixture was maintained at the same temperature for 5 minutes and cooled to −20° C. Then a solution of 215 mg (1 mmol, 96%) of allyl halide (II) in DMF (3 ml) was dropwise added thereto at the same temperature over 5 minutes and stirred for 3 hours. After the reaction, the resultant was poured into a saturated aqueous ammonium chloride solution and was extracted with ethyl acetate. The organic layer obtained was washed with a saturated aqueous sodium hydrogencarbonate solution and a saturated sodium chloride brine sequentially, and was dried with anhydrous magnesium sulfate. Thereafter, the solvent was removed by distillation, resulting in a crude yellow oil product. HPLC analysis showed that the yield of the sulfone (III) was 65.9%.

Example 4

To a solution of 585 mg of sulfone (I) in 6 ml of tetrahydrofuran was cooled to −60° C. was added dropwise 1.16 ml (1.2 mmol) of a tetrahydrofuran solution of sodium hexamethyldisilazide in a concentration of 0.96 mol/liter over 20 seconds and kept at the same temperature for 30 min. Then, a solution of 215 mg (1 mmol, purity 96%) of allyl halide (II) in tetrahydrofuran (3 ml) was dropwise added thereto over 5 min at the same temperature and stirred for 3 hours. After the reaction, the reaction solution was poured into an aqueous saturated sodium chloride solution and extracted with ethyl acetate. The obtained organic layer was washed with an aqueous saturated sodium hydrogencarbonate solution and an aqueous saturated sodium chloride solution in order and dried over anhydrous magnesium sulfate. Filtrate was evaporated to give a yellow oil product. HPLC analysis of the product showed the yield of the sulfone compound (III) was 70.0%.

Example 5

HPLC analysis of the obtained yellow oil product in this experiment showed that the yield of sulfone derivartive (III) was 59.4% by conducting the experiment in a similar manner as in Example 4 with the exception that 1.0 mol/liter THF solution of lithium diisopropyl amide was used in place of 0.96 mol/liter THF solution of the sodium hexamethyldisilazide.

Example 6

80 mg (2 mmol) of sodium hydride (60% oil suspension) was added to DMF(5 ml) and 88.9 mg (1.2 mmol) of sodium t-butoxide was added thereto and stirred at 50° C. for 2 hours. After a solution of 585 mg (2 mmol) of sulfone (I), and 4 mg (0.02 mmol) of 3,5-d-t-butyl-4-hydroxytoluene (BHT) in 3 ml of DMF was added thereto at the same temperature and stirred for 3 minutes and then cooled to −20° C., and a solution of 215 mg (1 mmol, purity 96%) of allyl halide (II) in DMF(2 ml) was added thereto in 1 minute and kept at the same temperature for 2 hours. After the reaction, the reaction solution was poured into an aqueous saturated ammonium chloride solution and extracted with ethyl acetate. The obtained organic layer was washed with an aqueous saturated sodium hydrogencarbonate solution and an aqueous saturated sodium chloride solution in this order, dried over anhydrous magnesium sulfate, and then filtrate was evaporated to give a crude yellow oil product. The obtained crude product was analyzed by HPLC to show that the yield of sulfone compound (III) was 59.5%.

Example 7

40 mg (1 mmol) of sodium hydride (60% oil suspension) was added to DMF(5 ml) and 99.1 mg (1 mmol) of sodium t-butoxide was added thereto and stirred at 40° C. After a solution of 585 mg (2 mmol) of sulfone (I), and 4 mg (0.02 mmol) of 3,5-d-t-butyl-4-hydroxytoluene (BHT) in 3 ml of DMF was added thereto at the same temperature and stirred for 20 minutes, and then cooled to −20° C. and stirred for 30 minutes, and a solution of 215 mg (1 mmol, purity 96%) of allyl halide (II) in DMF(2 ml) was added thereto in 1 minute and kept at the same temperature for 2 hours. After the reaction, the reaction solution was poured into an aqueous saturated ammonium chloride solution and extracted with ethyl acetate. The obtained organic layer was washed with an aqueous saturated sodium hydrogencarbonate solution and an aqueous saturated sodium chloride solution in this order, dried over anhydrous magnesium sulfate, and then filtrate was evaporated to give a crude yellow oil product. The obtained crude product was analyzed by HPLC to show that the yield of sulfone compound (III) was 59.6%.

Example 8

48 mg (1.2 mmol) of sodium hydride (60% oil suspension) was added to dimethyl sulfoxide (1 ml, DMSO) and stirred at room temperature for 3 hours. A solution of 585 mg (2 mmol) of sulfone (I) in DMSO (6 ml) was added dropwise thereto at the same temperature and stirred for 1 hour. Then a solution of 211 mg (1 mmol, purity 96%) of allyl halide (II) in DMSO(2 ml) was added dropwise thereto in 1 minute and kept at the same temperature for 5 minutes under stirring. After the reaction, water was added to the reaction solution and extracted with ethyl acetate. The obtained organic layer was washed with an aqueous saturated sodium hydrogencarbonate solution and an aqueous saturated sodium chloride solution in this order, dried over anhydrous magnesium sulfate, and then filtrate was evaporated to give a crude yellow oil product. The obtained crude product was analyzed by HPLC to show that the yield of sulfone compound (III) was 37.6%.

Example 9

To a solution of 116 mg (1.2 mmol) of sodium t-butoxide dissolved in DMF (6 ml) and cooled to 0° C. was added dropwise a solution of 585 mg (2 mmol) of sulfone (I) in DMF (4 ml) over 20 seconds and 22 mg (0.1 mmol) of 15-crown-5 was added thereto and kept for 5 minutes. A solution of 215 mg (1 mmol, purity 96%) of allyl halide (II) in DMF(4 ml) was added thereto in 5 minute and stirred at the same temperature for 3 hours. After the reaction, the reaction solution was poured into an aqueous saturated ammonium chloride solution and extracted with ethyl acetate. The obtained organic layer was washed with an aqueous saturated sodium hydrogencarbonate solution and an aqueous saturated sodium chloride solution in this order, dried over anhydrous magnesium sulfate, and then filtrate was evaporated to give a crude yellow oil product. The obtained crude product was analyzed by HPLC to show that the yield of sulfone compound (III) was 69.6%

Example 10

The experiment was conducted in a similar manner as in Example 9 except that 38 mg of tetrabutyl ammonium iodide was used in place of 15-crown-5. The obtained crude product was analyzed by HPLC to show that the yield of sulfone compound (III) was 65.2%.

Example 11

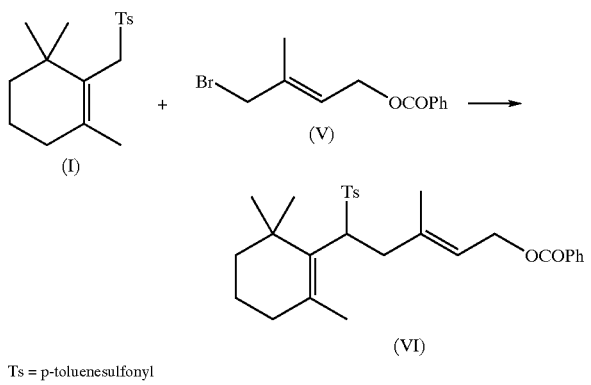

Ts = p-toluenesulfonyl

To a solution of 116 mg (1.2 mmol) of sodium t-butoxide dissolved in DMF (5 ml) and cooled to −20° C. was added dropwise a solution of 585 mg (2 mmol) of sulfone (I) in DMF (4 ml) and stirred for 5 minutes at the same temperature. After cooling the solution to −30° C., a solution of 269 mg (1 mmol) of allyl halide (V) in DMF (2 ml) was dropwise added thereto and stirred for 2.5 hours. After the reaction, water was added to the reaction solution and extracted with ethyl acetate. The obtained organic layer was washed with an aqueous saturated sodium hydrogencarbonate solution and an aqueous saturated sodium chloride solution in this order, dried over anhydrous magnesium sulfate, and then filtrate was evaporated to give a crude yellow oil product. The obtained crude product was purified by thin layer silica gel chromatography to give sulfone compound (VI) in a yield of 69.5%.
Sulfone (VI)
$^1$H-NMR δ (CDCl$_3$); 0.82(3H, s), 1.08(3H, s), 1.39(3H, s), 1.39–1.70(4H, m), 2.03(3H, s), 2.00–2.22(2H, m), 2.41 (3H, s), 2.68(1H, dd, J=7 Hz, 14 Hz), 3.05(1H, dd, J=7 Hz, 14 Hz), 3.93(1H, t, J=7 Hz), 4.70(2H, d, J=7 Hz), 5.51(1H, t, J=7 Hz), 7.27–8.04(9H, m)

Example 12

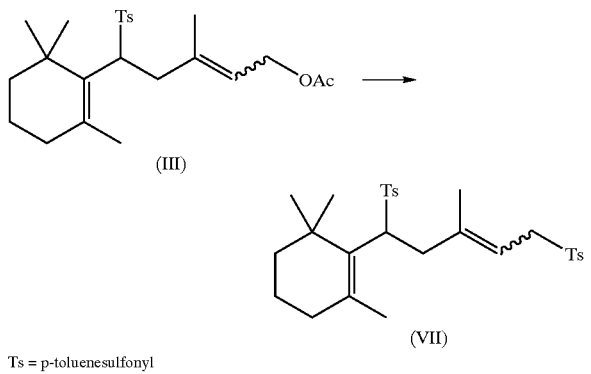

Ts = p-toluenesulfonyl 9 mg of palladium chloride (0.05 mmol), and 178 mg (1 mmol) of sodium p-toluenesulfinate were suspended in 2 ml of methanol under nitrogen atmosphere. After a solution of 62 mg (0.2 mmol) of triphenylphosphite and 211 mg (0.5 mmol, purity 98.3%) of sulfone(III) in tetrahydrofuran (2 ml) was added thereto and stirred for 1.5 hours at room temperature, the mixture was warmed to 60° C. and stirred for 5.5 hours. After the reaction, water and an aqueous saturated sodium chloride solution were poured thereto and extracted with ethyl acetate. The obtained organic layer was dried over anhydrous magnesium sulfate and filtered. The filtrate was evaporated to give a crude product. HPLC analysis of the product showed that the yield of allylsulfone compound (VII) was 89.1%.
Allyl Sulfone Drivative (VII)
0.75(3H*70/100, s), 0.98(3H*70/100, s), 0.78(3H*30/100, s), 1.00(3H*30/100, s), 1.15(3H, s), 1.26–1.61(7H, m), 1.98(3H*70/100, s), 2.00(3H*30/100, s), 2.44(3H, s), 2.55 (3H, s), 2.57–3.06(2H, m), 3.62–3.68(1H, m), 3.82–3.87 (1H, t, J=8 Hz), 5.18–5.23(1H, t, J=8 Hz), 7.26–7.35(4H, m), 7.66–7.78(4H, m)

Example 13

9 mg of palladium chloride (0.05 mmol), 54 mg (0.2 mmol) of triphenylphosphine, 250 mg (1 mmol) of sodium p-toluenesulfinate tetrahydrate, and 211 mg (0.5 mmol, purity 98.3%) of sulfone compound (III) were suspended in 3 ml of methanol and 3 ml of toluene and stirred at 60° C. for 4 hours. After the reaction, water was poured into the reaction mixture and extracted with ethyl acetate. The obtained organic layer was washed with an aqueous saturated ammonium chloride solution and an aqueous saturated sodium chloride solution in this order, and dried over anhydrous magnesium sulfate and filtered. The filtrate was evaporate to give a crude product. HPLC analysis of the product showed that the yield of allylsulfone compound (VII) was 78%.

Example 14

9 mg of palladium chloride (0.05 mmol), and 254 mg (1 mmol) of sodium p-toluenesulfinate tetrahydrate were suspended in methanol (1 ml). A solution of 52 (0.2 mmol)mg of triphenylphosphine, 211 mg (0.5 mmol, purity 98.3%) of sulfone compound (III) and 60 mg (1 mmol) of acetic acid in toluene (3 ml) was added thereto and stirred for 3 hours at 60° C. for 3 hours. After the reaction, water and an aqueous saturated sodium chloride solution were poured into the reaction mixture and extracted with ethyl acetate. The obtained organic layer was washed with an aqueous saturated ammonium chloride solution and an aqueous saturated sodium chloride solution in this order, and dried over anhydrous magnesium sulfate and filtered. The filtrate was evaporated to give a crude product. HPLC analysis of the product showed that the yield of allylsulfone compound (VII) was 76.9%.

Example 15

2.6 mg of palladium chloride (0.015 mmol), 156 mg (0.6 mmol) of triphenylphosphine, and 452 mg (1.8 mmol) of sodium p-toluenesulfinate tetrahydrate were suspended in methanol (1 ml), and 46 mg (0.45 mmol) of triethylamine and toluene 3 ml were added thereto and stirred at 60° C. at 10 hours. After the reaction, water was poured into the reaction mixture and extracted with ethyl acetate. The obtained organic layer was washed with an aqueous saturated ammonium chloride solution and an aqueous saturated sodium chloride solution in this order, and dried over anhydrous magnesium sulfate and filtered. The filtrate was evaporated to give a crude product. HPLC analysis of the product showed that the yield of allylsulfone compound (VII) was 74%.

Example 16

4.9 mg of palladium chloride (0.028 mmol), 151.6 mg (0.61 mmol) of sodium p-toluenesulfinate tetrahydrate, 211.9 mg (99.6%, 0.5 mmol) of sulfone compound (III), 124.3 mg (0.2 mmol) of tris(tridecyl)phosphite and 16.2 mg (0.16 mmol) of triethylamine were dissiolved in methanol (1 ml) and toluene (3 ml) and stirred at 60° C. for 6 hours. After the reaction, water was poured into the reaction mixture and extracted with ethyl acetate. The obtained organic layer was washed with an aqueous saturated ammonium chloride solution and an aqueous saturated sodium chloride solution in this order, and dried over anhydrous magnesium sulfate and filtered. The filtrate was evaporated to give a crude product. HPLC analysis of the product showed that the yield of allylsulfone compound (VII) was 83%.

Example 17

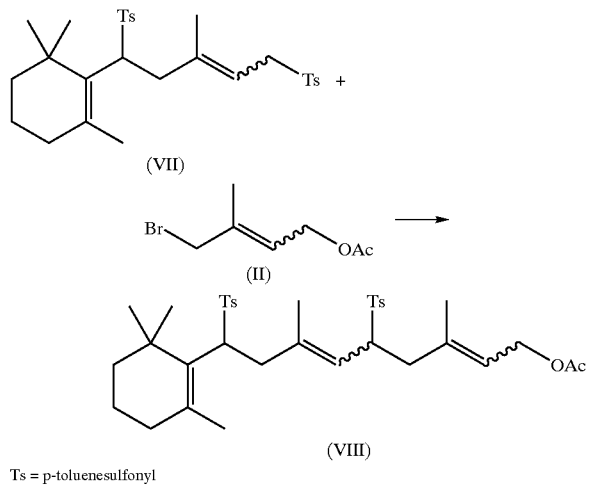

Ts = p-toluenesulfonyl

A solution of 47 mg (0.49 mmol) of sodium t-butoxide in DMF (6 ml) was cooled to 0° C. and a solution of 196 mg (0.38 mmol) of allyl sulfone compound (VII) in DMF (3 ml) was dropwise added thereto in 5 seconds and maintained at the same temperature for 2 minutes. Then, the reaction mixture was cooled to −60° C. and 88 mg (0.41 mmol, purity 96%) of allyl halide (II) in DMF (3 ml) was dropwise added thereto in 20 seconds and stirred for 3 hours. After reaction, the reaction mixture was poured into an aqueous saturated ammonium chloride solution and extracted with ethyl acetate. The obtained organic layer was washed with an aqueous saturated sodium hydrogencarbonate solution and an aqueous saturated sodium chloride solution in this order. The solution was dried over anhydrous magnesium sulfate and filtered. The filtrate was evaporated to give a crude yellow product, which was analyzed by HPLC to show that the yield of disulfone (VIII) was 92.8%.

Disulfone Compound (VIII)

$^1$H-NMR δ (CDCl$_3$); 0.66–1.69(21H, m), 1.91–2.04(3H, m), 1.91–2.04(2H, m), 2.43(3H, s), 2.45(3H, s), 2.52–3.11 (2H, m), 3.58–3.94(2H, m), 4.35–4.50(2H, m), 4.86–4.94 (1H, m), 5.18–5.38(1H, m), 7.28–7.39(4H, m), 7.65–7.79 (4H, m)

Example 18

19 mg (0.48 mmol) of sodium hydride (60%, oil suspension) was dissolved in DMF (6 ml) and cooled to 0° C. A solution of 190 mg (0.37 mmol) of allyl sulfone compound (VII) in DMF (3 ml) was dropwise added thereto over 20 seconds and maintained for 20 minutes. Then, a solution of 88 mg (0.41 mmol purity 96%) of allyl halide (II) in DMF (3 ml) was dropwise added thereto in 5 minutes and allowed to stand at room temperature under stirring for 3 hours. After reaction, the reaction mixture was poured into an aqueous saturated ammonium chloride solution and extracted with ethyl acetate. The obtained organic layer was washed with an aqueous saturated sodium hydrogencarbonate solution and an aqueous saturated sodium chloride solution in this order. The solution was dried over anhydrous magnesium sulfate and filtered. The filtrate was evaporated to give a crude yellow product, which was analyzed by HPLC to show that the yield of disulfone (VIII) was 94.8%.

Example 19

To a solution of 21 mg (0.53 mmol) of sodium hydroxide and 4.5 mg 0.02 mmol) of benzyltriethylammonium chloride in DMF (6 ml) was dropwise added a solution of 211 mg (0.41 mmol) of allyl sulfone compound (VII) in DMF (3 ml) at room temperature in 20 seconds and maintained at the same temperature for 20 minutes. Then a solution of 88 mg (0.41 mmol, purity 96%) of allyl halide (II) in DMF (3 ml) was dropwise added thereto over 20 seconds and stirred for 3 hours. After reaction, the reaction mixture was poured into an aqueous saturated ammonium chloride solution and extracted with ethyl acetate. The obtained organic layer was washed with an aqueous saturated sodium hydrogencarbonate solution and an aqueous saturated sodium chloride solution in this order. The solution was dried over anhydrous magnesium sulfate and filtered. The filtrate was evaporated to give a crude yellow product, which was analyzed by HPLC to show that the yield of disulfone (VIII) was 60.8%.

Example 20

To a solution of 46 mg (0.82 mmol) of potassium hydroxide and 4.5 mg (0.02 mmol) of benzyltriethylammonium chloride in DMF (6 ml), which was cooled to 0° C., was dropwise added a solution of 211 mg (0.41 mmol) of allyl sulfone compound (VII) in DMF (3 ml) at room temperature in 20 seconds and maintained at the same temperature for 20 minutes. Then a solution of 88 mg (0.41 mmol, purity 96%) of allyl halide (II) in DMF (3 ml) was dropwise added thereto over 20 seconds and stirred for 3 hours. After reaction, the reaction mixture was poured into an aqueous saturated ammonium chloride solution and extracted with ethyl acetate. The obtained organic layer was washed with an aqueous saturated sodium hydrogencarbonate solution and an aqueous saturated sodium chloride solution in this order. The solution was dried over anhydrous magnesium sulfate and filtered. The filtrate was evaporated to give a crude yellow product, which was analyzed by HPLC to show that the yield of disulfone (VIII) was 68.1%.

Example 21

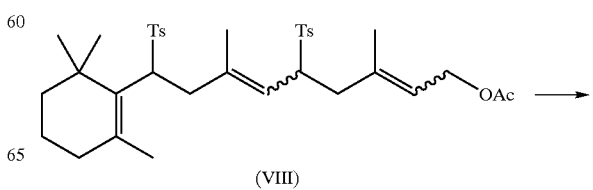

-continued

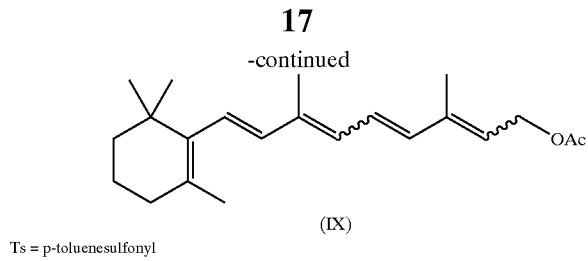

Ts = p-toluenesulfonyl

To a solution of 192 mg (0.3 mmol) of disulfone compound (VIII) in toluene (2 ml, BHT content: 300 ppm) was added 500 mg (9 mmol) of 95% potassium hydroxide, 19 mg of methanol (0.6 mmol), and 3 mg (0.015 mmol) of benzyltriethylammonium chloride were added thereto and stirred for 1 hour at 30° C. After the reaction, an aqueous saturated sodium chloride solution was poured into the reaction mixture and extracted with ethyl acetate, The obtained organic layer was washed with water, an aqueous saturated sodium chloride solution in this order and dried over anhydrous sodium sulfate. The dried solution was filtered and evaporated to give a crude retinol as a reddish oil. The obtained crude retinol was acetylated by a conventional manner and analyzed by HPLC to show that the yield of retinol acetate (IX) was 63.3%.

Example 22

To a solution of 256 mg (0.4 mmol) of disulfone compound (VIII) in hexane (2 ml, BHT content: 300 ppm) were added 240 mg (4 mmol) of 95% potassium hydroxide, 7 mg of methanol (0.2 mmol), and 4 mg (0.02 mmol) of benzyltriethylammonium chloride and stirred for 18 hours at 30° C. After the reaction, an aqueous saturated sodium chloride solution was poured into the reaction mixture and extracted with ethyl acetate. The obtained organic layer was washed with water, an aqueous saturated sodium chloride solution in this order and dried over anhydrous sodium sulfate. The dried solution was filtered and evaporated to give a crude retinol as a reddish oil. The obtained crude retinol was acetylated by a conventional manner and analyzed by HPLC to show that the yield of retinol acetate (IX) was 91.3%.

Example 23

To a solution of 256 mg (0.4 mmol) of disulfone compound (VIII) in toluene (2 ml, BHT content: 300 ppm) was added 240 mg (4 mmol) of 95% potassium hydroxide, 27 mg of methanol (0.8 mmol), and 4 mg (0.02 mmol) of benzyltriethylammonium chloride were added thereto and stirred for 11 hours at 40° C. After the reaction, an aqueous saturated sodium chloride solution was poured into the reaction mixture and extracted with ethyl acetate. The obtained organic layer was washed with water, an aqueous saturated sodium chloride solution in this order and dried over anhydrous sodium sulfate. The dried solution was filtered and evaporated to give a crude retinol as a reddish oil. The obtained crude retinol was acetylated by a conventional manner and analyzed by HPLC to show that the yield of retinol acetate (IX) was 89.3%.

Example 24

To a solution of 256 mg (0.4 mmol) of disulfone compound (VIII) in diisopropyl ether (2 ml, BHT content: 300 ppm) was added 240 mg (4 mmol) of 95% potassium hydroxide, 27 mg of methanol (0.8 mmol), and 4 mg (0.02 mmol) of benzyltriethylammonium chloride were added thereto and stirred for 16 hours at 30° C. After the reaction, an aqueous saturated sodium chloride solution was poured into the reaction mixture and extracted with ethyl acetate. The obtained organic layer was washed with water, an aqueous saturated sodium chloride solution in this order and dried over anhydrous sodium sulfate. The dried solution was filtered and evaporated to give a crude retinol as a reddish oil. The obtained crude retinol was acetylated by a conventional manner and analyzed by HPLC to show that the yield of retinol acetate (IX) was 94.7%

What is claimed is:

1. A disulfone compound of formula (1):

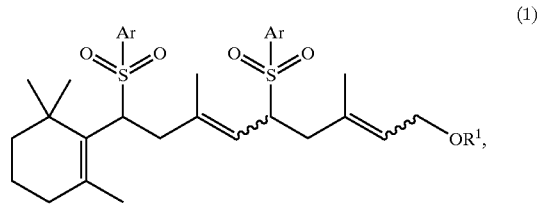

wherein Ar denotes a substituted or unsubstituted aryl group, $R^1$ denotes a hydrogen atom or a protective group of a hydroxyl group and the wavy line means that the disulfone compound is an E or Z geometrical isomer or a mixture thereof.

2. A process for producing a disulfone compound of formula (1):

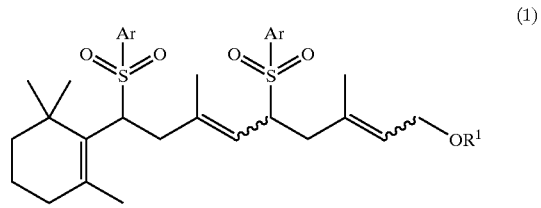

wherein Ar denotes a substituted or unsubstituted aryl group, R1 denotes a hydrogen atom or a protective group of a hydroxyl group and the wavy line means that the disulfone compound is an E or Z geometrical isomer or a mixture thereof, which comprises reacting an allylsulfone of formula (2):

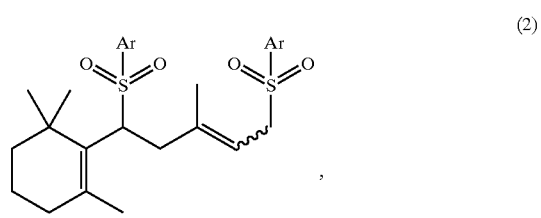

wherein Ar and the wavy line have the same meanings as defined in connection with formula (1) above, with an allyl halide compound of formula (3):

wherein X denotes a halogen atom, R denotes a protective group of a hydroxyl group and the wavy line has the same meanings as defined above, in the presence of a base selected from an alkyl lithium, an alkali metal alkoxide, an alkali metal amide, an alkali metal hydride, or an alkali metal hydroxide.

3. A process according to claim 2, which further comprises the step of reacting the disulfone compound of formula (1) with a base selected from an alkali metal hydride, an alkali metal alkoxide, an alkali metal amide, or an alkali metal hydroxide, and optionally deprotecting, to produce retinol.

4. A process for producing Retinol, which comprises reacting a disulfone compound of formula (1):

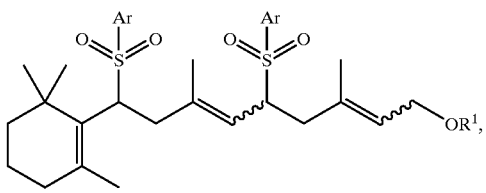
(1)

wherein Ar denotes an aryl group that may have a substituent, $R^1$ denotes a hydrogen atom or a protective group of a hydroxyl group and the wavy line means that the disulfone compound is an E or Z geometrical isomer or a mixture thereof, with a base selected from an alkali metal hydroxide, an alkali metal hydride, an alkali metal alkoxide or an alkali metal amide, and optionally deprotecting.

5. An allylsulfone compound of formula (2):

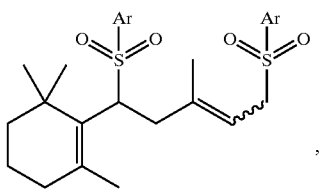
(2)

wherein Ar denotes a substituted or unsubstituted aryl group and the wavy line means that the allylsulfone compound is an E or Z geometrical isomer or a mixture thereof.

6. A process for producing an allylsulfone compound of formula (2):

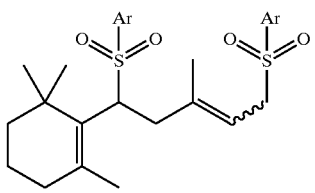
(2)

wherein Ar denotes a substituted or unsubstituted aryl group and the wavy line means that the allylsulfone compound is an E or Z geometrical isomer or a mixture thereof, which comprises reacting, in the presence of a palladium catalyst, a sulfone compound of formula (4):

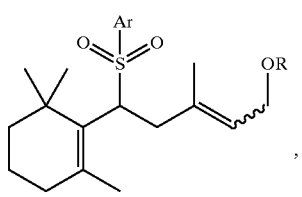
(4)

wherein R denotes a protective group of a hydroxyl group, and Ar and the wavy line have the same meanings as defined above, with an arylsulfinate of formula (5):

ArSO$_2$M (5)

wherein Ar has the same meaning as defined above and M denotes an alkali metal.

7. A process according to claim 6, which further comprises the steps of (a) reacting the allylsulfone compound of formula (2):

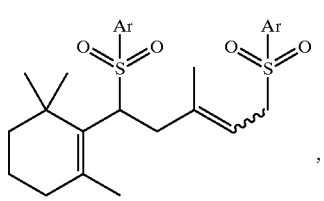
(2)

wherein Ar and the wavy line have the same meanings as defined in connection with formula (4), with an allyl halide compound of formula (3):

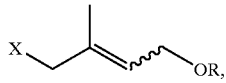
(3)

wherein X denotes a halogen atom, R denotes a protective group of a hydroxyl group and the wavy line has the same meanings as defined above, in the presence of a base selected from an alkyl lithium, an alkali metal alkoxide, an alkali metal amide, an alkali metal hydride, or an alkali metal hydroxide, to produce a disulfone compound of formula (1):

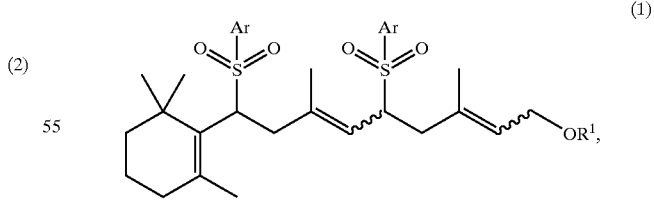
(1)

wherein Ar denotes a substituted or unsubstituted aryl group, $R^1$ denotes a hydrogen atom or a protective group of a hydroxyl group and the wavy line means that the disulfone compound(1) is an E or Z geometrical isomer or a mixture thereof, and (b) reacting the disulfone compound of formula (1) with a base selected from an alkali metal hydroxide, an alkali metal hydride, an alkali metal alkoxide or an alkali metal amide, and optionally deprotecting, to produce retinol.

8. A process for producing a sulfone of formula (4):

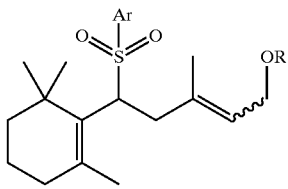
(4)

wherein R denotes a protective group of a hydroxyl group, and Ar denotes a substituted or unsubstituted aryl group, R denotes a protective group of a hydroxy group, and the wavy line means that the sulfone compound is an E or Z geometrical isomer or a mixture thereof, which comprises reacting a sulfone of formula (6):

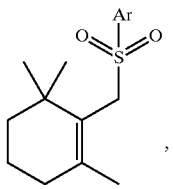
(6)

wherein Ar has the same meaning as defined above, with an allyl halide compound of formula (3):

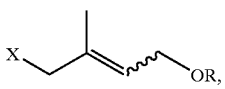
(3)

wherein X denotes a halogen atom, and R and the wavy line have the same meanings as defined above, in the presence of a base selected from an alkyl lithium, an alkali metal alkoxide, an alkali metal amide, or an alkali metal hydride.

9. A process according to claim 8, which further comprises the steps of (a) reacting the sulfone of formula (4), in the presence of a palladium catalyst, with an arylsulfinate of formula (5):

ArSO$_2$M    (5)

wherein Ar has the same meaning as defined above and M denotes an alkali metal, to produce an allylsulfone of formula (2):

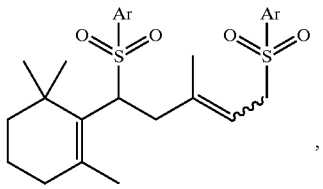
(2)

wherein Ar and the wavy line have the same meanings as defined in connection with formula (4), (b) reacting the allylsulfone of formula (2), with an allyl halide compound of formula (3):

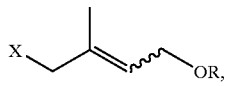
(3)

wherein X denotes a halogen atom, R denotes a protective group of a hydroxyl group and the wavy line has the same meanings as defined above, in the presence of a base selected from an alkyl lithium, an alkali metal alkoxide, an alkali metal amide, an alkali metal hydride, or an alkali metal hydroxide, to produce a disulfone compound of formula (1):

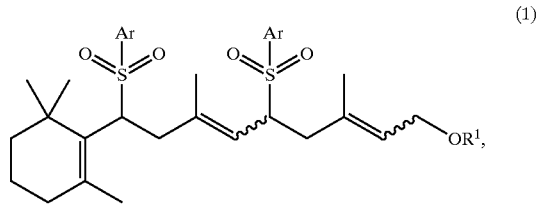
(1)

wherein Ar denotes a substituted or unsubstituted aryl group, $R^1$ denotes a hydrogen atom or a protective group of a hydroxyl group and the wavy line means that the disulfone compound is an E or Z geometrical isomer or a mixture thereof, and (c) reacting the disulfone compound of formula (1) with a base selected from an alkali metal hydroxide, an alkali metal hydride, an alkali metal alkoxide or an alkali metal amide, and optionally deprotecting, to produce retinol.

10. A process according to claim 3, wherein the disulfone compounds of formula (1) is reacted with the base in the presence of a phase transfer catalyst and a lower alcohol.

11. A process according to claim 10, wherein the phase transfer catalyst is a quaternary ammonium salt.

12. A process according to claim 11, wherein the quaternary ammonium salt is benzyltriethylammonium chloride.

13. A process according to claim 10, wherein the lower alcohol is methanol, ethanol, isopropanol or n-propanol.

14. A process according to claim 2, wherein the alkali metal alkoxide is sodium methoxide, potassium methoxide, lithium methoxide, sodium ethoxide, potassium ethoxide, lithium ethoxide, potassium t-butoxide, sodium t-butoxide, lithium t-butoxide, sodium t-amylate, or potassium t-amylate.

15. A process according to claim 2, wherein the alkali metal amide is lithium amide, potassium amide, sodium amide, lithium diisopropylamide, sodium hexamethyldisilazide, potassium hexamethyldisilazide, or lithium hexamethyldisilazide.

16. A process according to claim 2, wherein the alkali metal hydride is sodium hydride, potassium hydride, or lithium hydride.

17. A process according to claim 2, wherein the alkali metal hydroxide is lithium hydroxide, sodium hydroxide, or potassium hydroxide.

18. A process according to claim 3, wherein the alkali metal alkoxide is sodium t-butoxide or potassium t-butoxide.

19. A process according to claim 2, wherein the R in the allyl halide compound of formula (3) is an acyl group.

20. A process according to claim 19, wherein R in the allyl halide compound of formula (3) is an acetyl group.

21. A process according to claim 6, wherein the arylsulfinate of formula (5) is reacted in the presence of a palladium catalyst and a phosphorus ligand.

22. A process according to claim 21, wherein the reaction of the arylsulfinate of formula (5) is conducted in the presence of a palladium catalyst, a phosphorous ligand and an amine compound.

23. A process according to claim 21, wherein the reaction of the arylsulfinate of formula (5) is conducted in the presence of a palladium catalyst, a phosphorous ligand and an acid compound.

24. A process according to claim 22, wherein the amine compound is a mono-, di-, or tri-(C2–C6)alkyl-amine, a secondary or tertiary cyclic amine, a primary, secondary or tertiary aryl amine.

25. A process according to claim 22, wherein the amine compound is ethylamine, n-propylamine, isopropylamine, n-butylamine, sec-butylamine, t-butylamine, n-pentylamine, n-hexylamine, cyclohexylamine, aniline, o-, m-, or p-anisidine, 4-n-butylaniline, diethylamine, diisopropylamine, di-n-butylamine, di-n-hexylamine, pyrrolidine, piperidine, morpholine, N-methylaniline, N-ethylaniline, N-n-butylaniline, N-methyl-p-anisidine, diphenylamine, triethylamine, tri-n-propylamine, triisopropylamine, N,N-diisopropylethylamine, tri-n-butylamine, triisobutylamine, tri-n-pentylamine, tri-n-hexylamine, N-methylpyrrolidine, N-methylpiperidine, N-ethylpiperidine, N-methylmorpholine, triphenylamine, or ethylenediamine,N,N,N'N'-tetramethylethylenediamine.

26. A process according to claim 23, wherein the acid compound is a carboxylic acid.

27. A process according to claim 26, wherein the carboxylic acid compound is formic acid, acetic acid, propionic acid, oxalic acid, benzoic acid, p-nitrobenzoic acid, or p-chlorobenzoic acid.

28. A process according to claim 21, wherein the arylsulfinate is sodium phenylsufinate, potassium phenylsulfinate, sodium p-toluenesulfinate or potassium p-toluenesulfinate.

29. A process according to claim 6, wherein R in the compound of the formula (4) is an acyl group.

30. A process according to claim 29, wherein the acyl group is an acetyl group.

* * * * *